(12) United States Patent
Zeldov et al.

(10) Patent No.: US 10,481,174 B2
(45) Date of Patent: Nov. 19, 2019

(54) SUPERCONDUCTING SCANNING SENSOR FOR NANOMETER SCALE TEMPERATURE IMAGING

(71) Applicant: YEDA RESEARCH AND DEVELOPMENT CO. LTD., Rehovot (IL)

(72) Inventors: Eli Zeldov, Rehovot (IL); Lior Embon, Rehovot (IL); Dorri Halbertal, Rehovot (IL); Yonathan Anahory, Rehovot (IL); Yuri Myasoedov, Rehovot (IL); Jo Cuppens, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 53 days.

(21) Appl. No.: 15/557,104

(22) PCT Filed: Mar. 10, 2016

(86) PCT No.: PCT/IL2016/050262
§ 371 (c)(1),
(2) Date: Sep. 10, 2017

(87) PCT Pub. No.: WO2016/142945
PCT Pub. Date: Sep. 15, 2016

(65) Prior Publication Data
US 2018/0045754 A1 Feb. 15, 2018

Related U.S. Application Data

(60) Provisional application No. 62/131,419, filed on Mar. 11, 2015.

(51) Int. Cl.
*G01Q 60/58* (2010.01)
*G01K 7/00* (2006.01)
*G01N 27/04* (2006.01)

(52) U.S. Cl.
CPC ............. *G01Q 60/58* (2013.01); *G01K 7/006* (2013.01); *G01K 2203/00* (2013.01); *G01N 27/041* (2013.01)

(58) Field of Classification Search
CPC .... G01Q 60/58; G01K 7/006; G01K 2203/00; G01N 27/041
(Continued)

(56) References Cited

U.S. PATENT DOCUMENTS 4,747,698 A * 5/1988 Wickramasinghe ... G01N 25/72
136/228
5,627,815 A   5/1997 Koyanagi et al.
(Continued)

FOREIGN PATENT DOCUMENTS

WO   WO 2014/129896 A1   8/2014
WO   WO 2014/188416 A1   11/2014

OTHER PUBLICATIONS

Ho et al. "A scanning thermocouple probe for temperature mapping" IEEE Transactions on Instrumentation and Measurement. Oct. 2001;50(5):1167-70.
(Continued)

Primary Examiner — Michael Maskell
(74) Attorney, Agent, or Firm — Mark S. Cohen; Pearl Cohen; Zedek Latzer Baratz LLP

(57) ABSTRACT

A device and methods for use thereof in low-temperature thermal scanning microscopy, providing non-contact, non-invasive localized temperature and thermal conductivity measurements in nanometer scale ranges with a temperature resolution in the micro-Kelvin order. A superconductive cap
(Continued)

mounted on the tip of an elongated support probe is electrically-connected to superconductive leads for carrying electrical current through the cap. The critical superconducting current of the leads is configured to be greater than the critical current supported by the cap, and the cap's critical current is configured to be a function of its temperature. Thus, the temperature of the cap is measured by measuring its critical superconducting current. In a related embodiment, driving a current greater than the critical current of the cap quenches the cap's superconductivity, and permits the cap to dissipate resistive heat into the sample being scanned. Scanning of the sample in this mode thus images its thermal conductivity patterns.

33 Claims, 12 Drawing Sheets

(58) Field of Classification Search
 USPC .............................. 850/50, 56, 57
 See application file for complete search history.

(56) References Cited

U.S. PATENT DOCUMENTS

| 5,929,438 | A  | * | 7/1999  | Suzuki ............... | B82Y 35/00 |
|           |    |   |         |                      | 136/228    |
| 6,215,137 | B1 | * | 4/2001  | Suzuki ............... | B82Y 35/00 |
|           |    |   |         |                      | 257/253    |
| 7,262,066 | B2 |   | 8/2007  | McNamara et al.      |            |
| 7,553,335 | B2 | * | 6/2009  | Tanda ................ | B82Y 15/00 |
|           |    |   |         |                      | 250/306    |
| 8,914,911 | B2 | * | 12/2014 | King ................. | B82Y 35/00 |
|           |    |   |         |                      | 73/105     |
| 2004/0145366 | A1 | | 7/2004 | Baudenbacher et al.  |            |
| 2006/0254345 | A1 | * | 11/2006 | King ................ | B82Y 35/00 |
|           |    |   |         |                      | 73/105     |
| 2007/0085002 | A1 | | 4/2007 | Yao et al.           |            |
| 2009/0056428 | A1 | * | 3/2009 | King ................ | B82Y 35/00 |
|           |    |   |         |                      | 73/105     |
| 2009/0114000 | A1 | | 5/2009 | Hecker et al.        |            |
| 2010/0207622 | A1 | | 8/2010 | Finkler et al.       |            |
| 2011/0078834 | A1 | * | 3/2011 | King ................ | G01K 1/143 |
|           |    |   |         |                      | 850/9      |
| 2012/0054924 | A1 | * | 3/2012 | Zhang ............... | G01Q 60/58 |
|           |    |   |         |                      | 850/6      |
| 2013/0019352 | A1 | * | 1/2013 | Liu .................. | G01Q 60/58 |
|           |    |   |         |                      | 850/50     |
| 2013/0019353 | A1 | * | 1/2013 | Liu .................. | G01Q 60/58 |
|           |    |   |         |                      | 850/50     |
| 2013/0047303 | A1 | * | 2/2013 | King ................ | B82Y 35/00 |
|           |    |   |         |                      | 850/56     |
| 2014/0203707 | A1 | * | 7/2014 | King ................ | H01J 9/02  |
|           |    |   |         |                      | 315/111.81 |

OTHER PUBLICATIONS

International Search Report for PCT Application No. PCT/IL2016/050262 dated Jul. 6, 2016.

Janus et al. "Novel SThM nanoprobe for thermal properties investigation of micro—and nanoelectronic devices" Microelectronic Engineering. May 1, 2010;87(5-8):1370-4.

Kim et al. "Observation of a linear temperature dependence of the critical current density in a $Ba_{0.63}K_{0.37}BiO_3$ single crystal" Physica C: Superconductivity. Nov. 1, 2000;341:729-30.

Pekola J. "Trends in thermometry" Journal of low temperature physics. Jun. 1, 2004;135(5-6):723-44.

Supplementary European Search Report for European Application No. EP16761207.6 dated Sep. 7, 2018.

Vasyukov et al. "A scanning superconducting quantum interference device with single electron spin sensitivity" Nature nanotechnology. Sep. 2013;8(9):639.

* cited by examiner

SUPERCONDUCTING SCANNING SENSOR FOR NANOMETER SCALE TEMPERATURE IMAGING

CROSS-REFERENCE TO RELATED APPLICATIONS

This application is a National Phase Application of PCT International Application No. PCT/IL2016/050262, International Filing Date Mar. 10, 2016, claiming priority of U.S. Provisional Patent Application No. 62/131,419, filed Mar. 11, 2015, which are hereby incorporated by reference.

TECHNOLOGICAL FIELD

The present invention is in the field of temperature measurement devices and thermal imaging on nanometer length scales.

BACKGROUND ART

References considered to be relevant as background to the presently disclosed subject matter are listed below:
(1) H. P. Ho, K. C. Lo, and S. Y. Wu. A scanning thermocouple probe for temperature mapping. *Instrumentation and Measurement, IEEE Transactions on*, 50(5):1167-1170, 2001.
(2) P. Janus, D. Szmigiel, M. Weisheit, G. Wielgoszewski, Y. Ritz, P. Grabiec, M. Hecker, T. Gotszalk, P. Sulecki, and E. Zschech. Novel SThM nanoprobe for thermal properties investigation of micro- and nanoelectronic devices. *Microelectronic Engineering*, 87(5): 1370-1374, 2010.
(3) D. Vasyukov, Y. Anahory, L. Embon, D. Halbertal, J. Cuppens, L. Neeman, A. Finkler, Y. Segev, Y. Myasoedov, M. L. Rappaport, M. E. Huber, and E. Zeldov. A scanning superconducting quantum interference device with single electron spin sensitivity. *Nature Nanotechnology*, 8:639-644, 2013.

Acknowledgement of the above references herein is not to be inferred as meaning that these are in any way relevant to the patentability of the presently disclosed subject matter.

BACKGROUND

Mapping thermal properties and temperature of a sample may be used for various inspection and quality assurance of materials and devices (e.g. electronic devices). Various types of scanning probe microscopy are known in the art, utilizing corresponding probe configuration and measurement methods to provide mapping of desired characteristics of the scanned sample. Some of the best known techniques include the scanning tunneling microscopy (STM) and atomic force microscopy (AFM) typically providing information of surface structure of a scanned substrate.

Additional probe configurations as well as operations techniques have been used for mapping substrates based on selected characteristics thereof. For example, U.S. Pat. No. 8,723,514, as well as published PCT application WO/2014/188416, describing a sensor device (e.g. probe) utilizing superconductors to provide Josephson junction(s) based sensor providing measurements data indicative of magnetic fields in vicinity of the sensor. Such sensor configurations allows for scanning magnetic imaging of a substrate.

Additional scanning methods are known, including scanning thermal microscope techniques, configured to provide thermal mapping of the scanned substrate. For example, U.S. Pat. No. 7,262,066 describes systems and methods for identifying characteristics and defects in material such as semiconductors. Methods include scanning with a thermal probe in the vicinity of a semiconductor sample, applying stimuli to the thermal probe, and monitoring the interaction of the thermal probe and the semiconductor. The stimulus can be applied by a variety of methods, including Joule heating of a resistor in the proximity of the probe tip, or optically heating a tip of the thermal probe using a laser. Applications of the invention include identification of voids in metallic layers in semiconductors; mapping dopant concentration in semiconductors; measuring thickness of a sample material; mapping thermal hot spots and other characteristics of a sample material.

General Description

There is a need in the art for a novel technique for use in thermal imaging of a substrate. The present invention provides a device and technique for thermal scanning microscopy providing non-contact localized thermal measurements within a desired range of temperatures.

Thermal imaging at low temperatures provides various challenges. Unlike relatively high temperature systems (e.g. room temperature) providing thermal emission of measurable electromagnetic radiation, providing thermal map of low temperature systems requires direct contact between a probe and different point of the system being measured. Such direct contact is required in order to allow local thermal equilibration between the probe and the measured point in the system and thus enable measurement of the local sample temperature. This may also cause interference with characteristics of the system such as coherence, and may in some cases damage the system.

It should be noted that the currently available techniques for thermal scanning microscopy generally utilize direct physical contact between surface of the substrate and a metallic end of a scanning probe. This is to allow localize heat transfer between the substrate and the probe and thus enable measuring of the probe temperature by means of thermocouple, resistance variation etc. Additional heat transfer mechanisms, such as heat transfer through liquid drops forming at the contact point or through gas exchange between the probe and substrate, are minimized to prevent non-local effects on the measurement.

Thus, differently from the conventional techniques, the present invention provides thermal measurements (temperature variation) of a sample while eliminating, or at least significantly reducing, contact between the measuring probe and the substrate. Thus, the present invention provides a non-invasive thermal measurement device suitable for providing information about temperature distribution on a sub-micrometer scale avoiding any physical contact or interaction with the measured substrate. Heat transfer between the substrate and the probe may be provided by low pressure inert gas sustaining desired conditions in the measurement environment.

The predetermined configuration of the probe in combination with appropriate measurement technique allow for determining local temperature of a sample while avoiding any physical contact with its surface. Moreover, the technique of the invention allows imaging of the local temperature variations of the sample with nano-metric spatial resolution and temperature resolution of the order of $\mu K$ (micro-Kelvin) above a constant background temperature of a few K. It should be noted that such temperature sensitivity may be about 3 orders of magnitude better than any of the thermal scanning technique and systems known to date, which are limited to temperature resolutions of several mK (milli-Kelvin) at best. Commercially available thermal scanning systems show even worse temperature resolution, and are limited to an order of 100 mK. It should also be noted that the currently available scanning thermal microscopy techniques are limited in operation at cryogenic temperatures.

The term "probe" herein denotes a slender, elongated element having a proximal (or near) end for being held or mounted to a positioning or scanning apparatus; and a distal (or far) end for approaching or contacting a sample under examination. The term "tip" herein denotes the terminus of the far end. In certain embodiments, a probe functions as a support structure for sensor elements.

According to various embodiments of the present invention a superconductive cap is an active sensor element mounted on the tip of a probe or support structure. In these embodiments, the cap is electrically connected to at least two superconductive leads configured to transmit electrical current through the cap. The leads are spaced apart so that they are not in direct contact with one another.

It is understood that the cap and the leads have superconductive capabilities, but are not always necessarily in a superconducting state. In certain embodiments, however, the cap and leads are always electrically conductive, even when not in a superconducting state. Thus, in some descriptions that follow, the cap is referred to as an "electrically conductive cap", and the leads are referred to as "conductive leads"—it being understood that under proper predetermined conditions the "electrically conductive cap" and/or the "conductive leads" are in a superconducting state. It is also understood that the term "conductive" when appearing herein without further qualification relates to the conducting of an electrical current.

The cap and leads are configured with selected material composition and geometry to support predetermined levels of critical current. Desired levels of critical current may be selected such that the cap is configured to support a first level of critical current; the leads are configured to support a second level of critical current that is greater than the first critical current. In a related embodiment, the cap is considered to be an integral part of the tip or support structure. In another related embodiment, the leads are considered to be an integral part of the probe or support structure.

According to embodiments of the present invention, the thermal measurement technique relies on the dependency of critical current in a superconductive material on temperature. To measure the cap temperature, current is transmitted through the leads to the cap. As long as the cap is superconducting, there is effectively no resistance to this current transmission. When the transmitted current through the cap is higher than the corresponding critical current, the superconducting state of the cap is suppressed and it shows resistance to current transmission.

The probe/sensor of the present invention as described further below provides extremely high sensitivity in thermal measurements, thereby allowing detection while avoiding contact with a sample being measured. It should however be noted that the probe may be used for contact thermal measurements utilizing direct heat transfer between the sample and the cap. Such contact measuring scheme may be used to further improve thermal sensitivity as well as when there is no risk of physical damage to the sample. Thus, it should be noted that the probe of the invention may be used for thermal measurements (e.g. thermal scanning microscopy) in contact and non-contact embodiments. According to a contact measurement embodiment, heat transfer between the cap and the sample is provided by direct physical contact between them. According to a non-contact embodiment, heat transfer is provided by an exchange gas under a predetermined pressure, which is introduced into the measurement chamber.

An embodiment of the present invention provides a system and a technique for obtaining localized temperature information on a sub-micrometer scale while eliminating, or at least significantly reducing, any interaction with the measured system. The thermal probe of the embodiment allows thermal imaging of a system in the form of scanning microscopy in significantly improved sensitivity and bandwidth.

Thus, according to an embodiment of the invention, there is provided a device for use in thermal microscopy, wherein the device includes:
an elongated support structure having a near end for attachment to external connection and a far end;
an electrically conductive cap located at the far end of the support structure;
at least two elongated conductive leads extending from the electrically conductive cap along the support structure to the near end thereof and in electrical contact with the electrically conductive cap.

In addition, according to another embodiment of the invention, there is provided a method for thermal imaging a sample, the method including:
providing a superconductive cap on the tip of an elongated probe, the superconductive cap having a first critical current value and being in close proximity to the sample; and
transmitting an electrical current through the cap to determine a variation in a critical current thereof, the variation in the critical current being indicative of a local temperature of the sample.

The electrically conductive cap and at least two elongated conductive leads provide a path for transmission of electric current through the cap. In certain related embodiments, the electrically conductive cap and elongated conductive leads are configured from selected material compositions such as to be in a superconducting state at predetermined conditions, i.e. superconductive cap and leads selected for type I or type II superconductors. When in the superconducting state, the cap is configured to support a first critical current and the leads are configured to support a second critical current. According to various embodiments, the second critical current is greater than the first critical current. This can be achieved by proper material selection of the cap and the leads. In certain embodiments, this is achieved utilizing geometry variations. In a non-limiting example, the electrically conductive cap is configured with a first cross section along the path of electrical current and the elongated conductive leads are configured with a second cross section along the path of electrical current, where the second cross section has greater area than the first cross section.

It should be noted that generally, to provide high resolution thermal scanning microscopy; the device may be of nanometric dimension. For example, the electrically conductive cap may be configured with a diameter of less than 300 nm, or less than 100 nm.

According to some embodiments, the elongated support structure is configured as conical structure. Additionally or alternatively, the elongated support structure may be configured from pulled quartz rod.

According to yet another broad aspect of the invention, there is provided a sensor device comprising a probe carrying a non-invasive thermal sensor; the probe comprising: a support structure configured to be carried by connection to a near end thereof and carrying a superconductive cap attached to a far end thereof, and at least two elongated superconductive leads connected to the superconductive cap at a far end thereof and providing corresponding electrically conductive ports at near end to thereby allow current transmission to the cap; wherein the superconductive cap having a first critical current value and the superconductive leads having a second critical current value being higher than the first critical current value.

The sensor device may be configured to provide thermal measurements of a sample while having the cap at a distance larger than 10 nanometers from the sample; in some embodiments, the device may be configured to provide thermal measurements of a sample while having the cap at a distance larger than 1 micro-meter from the sample.

According to further embodiments of the invention, there is provided a system including a scanning unit carrying a sensor probe, the scanning unit is configured to selectively move the probe along a surface of a sample; the sensor probe including an elongated support structure carried on a near end thereof by the scanning unit and carrying a conductive cap on a far end thereof, and at least two elongated conductive leads electrically connected to the cap; wherein the sensor probe being configured for thermal measurements of surface of the sample. In related embodiments, the sensor probe is configured for thermal measurements of the surface of the sample while avoiding physical contact with the surface.

The scanning unit may be configured for holding the probe at a fixed location and varying location of a sample holder configured for carrying the sample, or holds the sample on the sample holder at a fixed location and varying location of the probe with respect to the sample.

The system may further include a vacuum chamber configured for holding the sample to be scanned and performing the scan therein.

The sensor probe may be configured to determined temperature variation of the sample in cryogenic temperatures range.

According to some embodiments, transmitting electrical current through the cap includes gradually increasing the electrical current to determine critical current value of the cap by detecting resistance to current flow through the cap. In other embodiments, transmitting electrical current through the cap to determine variation in critical current thereof includes transmitting a fixed current through the probe and determining the critical current based on portion of current flowing through the cap.

It should be noted that the close proximity may indicate scanning distance greater than 10 nm from the sample.

According to some embodiments, the method may further comprise inducing periodical thermal variation to the sample and periodically detecting the critical current of the superconductive cap to determine amplitude and phase data indicative of temperature and heat propagation in the sample. The periodically detecting of the critical current may comprise detecting the critical current at measurement frequency higher than 1 KHz, thereby providing thermal measurement at bandwidth greater than 1 KHz. In some embodiment, the measurement frequency may be greater than 100 KHz, or even greater than 10 MHz, increasing the thermal measurement bandwidth accordingly.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

Figure 1:
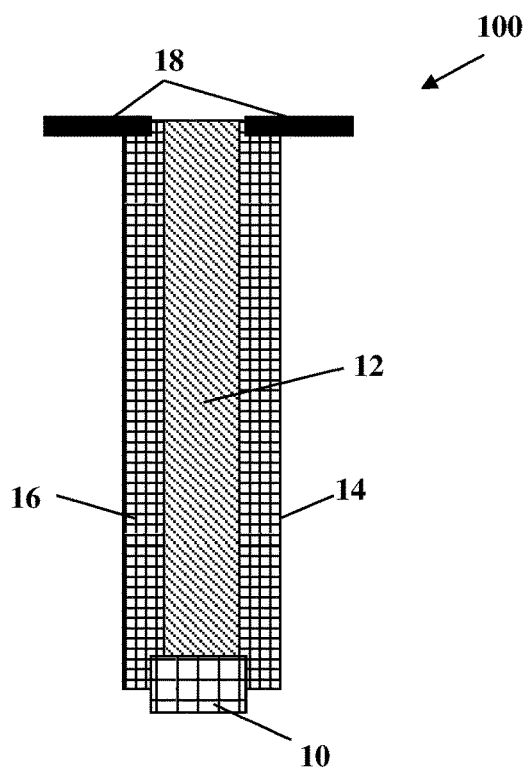
FIG. 1 illustrates a probe/sensor for use in thermal measurements according to some embodiments of the invention.

For simplicity and clarity of illustration, elements shown in the figures are not necessarily drawn to scale, and the dimensions of some elements may be exaggerated relative to other elements. In addition, reference numerals may be repeated among the figures to indicate corresponding or analogous elements.

DETAILED DESCRIPTION

As indicated above, temperature mapping of a physical system with nanometric-scale resolution may provide a powerful tool both for exploring basic physical phenomena as well as part of development and quality assessment of nanometric devices, being electronic and/or electromechanical or any other nanometric systems. Various types of scanning thermal microscopes (SThM) are known in the past decades utilizing different techniques for temperature measurements, such as thermocouple, thermoresistive films or wires, Schottky diodes etc. Such thermal sensors have been incorporated onto a tip of an atomic force microscope (AFM) to provide nanoscale thermal mapping of a sample. Currently, the state of the art SThM systems can reach a spatial resolution of 30 nm and thermal sensitivity of about $$\sim \frac{3 \text{ mK}}{\sqrt{\text{Hz}}}$$

and a bandwidth of up to 20 kHz. Additionally, due to the thermal sensor configuration, the currently available SThM systems are operable at ambient temperatures, e.g. room temperature and generally require physical contact between the thermal sensor tip and the surface of the sample to provide accurate measurement.

In this connection, the present invention provides a novel thermal measurement device, suitable for use in cryogenic thermal imaging with thermal sensitivities of the order of $$\frac{1 \text{ μK}}{\sqrt{\text{Hz}}}$$

Specifically, such temperature sensitivity provides detection of temperature variation of 1 micro-Kelvin within integration (measurement) time of 1 second. Reference is made to FIG. 1 schematically illustrating a sensor unit 100 according to some embodiments of the present invention. The sensor unit is in the form of a cap 10 having nanoscale dimension and located at a far end of an elongated support structure 12 (tip). The cap 10 is electrically connected to at least two elongated, electrically conductive leads 14 and 16 allowing transmission of electrical current from at least two corresponding ports 18.

The cap 10 and the elongated conductive leads 14 and 16 are configured of a material having superconducting properties at temperatures being under predetermined critical temperature. In this connection it should be noted that according to the technique of the present invention and as will be described further below, the thermal sensor 100 is generally operable at cryogenic temperatures, i.e. the sensor 100 is operable at temperature range in which the cap 10 and leads 14 and 16 are superconducting.

Preferably, the cap 10 and the corresponding conductive leads 14 and 16 are configured with material selection and geometry to support predetermined current density flowing therethrough. More specifically, the cap 10 is configured to support a first critical current and the leads 14 and 16 are configured to support a second critical current. The second critical current is selected to be higher than the first critical current. This can be achieved by forming the cap 10 with smaller cross section for current transmission with respect to the cross section of the leads 14, 16. Alternatively, this can be achieved by forming the cap 10 and the leads 14, 16 from selected materials having appropriate critical current densities.

The inventors of the present invention have found that the critical current density of a superconducting material depends highly on temperature of the material. Thus, small variations in the temperature of the material, e.g. temperature increase of a few micro-Kelvin, reduce the critical current density up to a measurable extent. Thus, scanning current transmission through the leads 14, 16 to the cap 10 to determine the value of critical current provides data indicative of cap temperature.

The thermal sensor/probe 100 as described above may be configured to enable non-contact thermal measurement of a sample. More specifically, operating in suitable thermal conditions to support the superconducting state of the cap 10, the sensor 100 can be used to detect local thermal fluctuations of a sample's surface from distances of tens of nanometers up to a few microns from the surface of the sample.

To provide such a thermal sensitivity, the sensor device is preferably mounted on a support structure having low thermal conductivity. Thus, the support structure 12 is preferably configured with cross section dimension smaller than mean-free path of phonons in the support structure 12 material. Additionally, the superconducting state of leads 14, 16 also contribute to the low thermal conductivity of the sensor device 100, generally rendering the leads as thermal isolators. This configuration provides thermally isolated cap 10 and thus enable detection of small thermal variations of the sample. It should be noted that the cap 10 is preferably configured with small (nanometric) dimension to provide high mapping resolution and high thermal response.

Figure 2A:
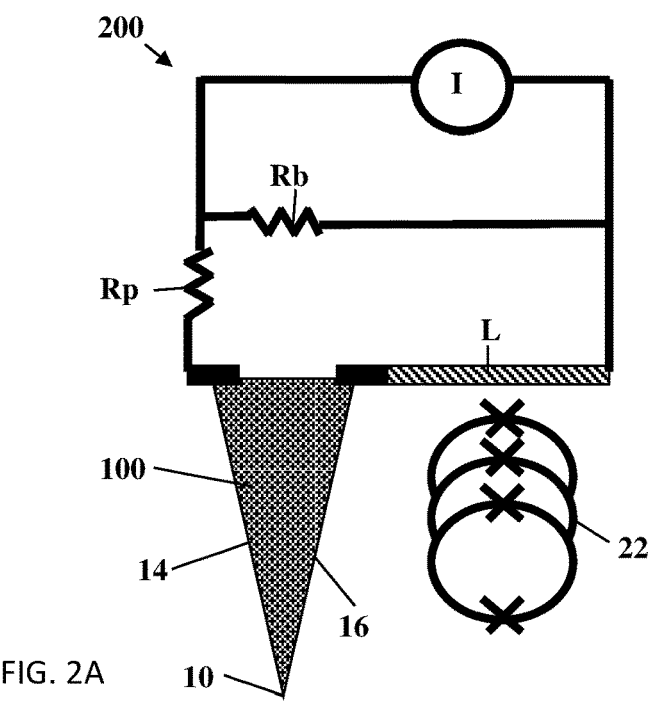
FIGS. 2A and 2B exemplify measuring circuit for use in thermal measurements according to some embodiments of the invention.
Figure 2B:
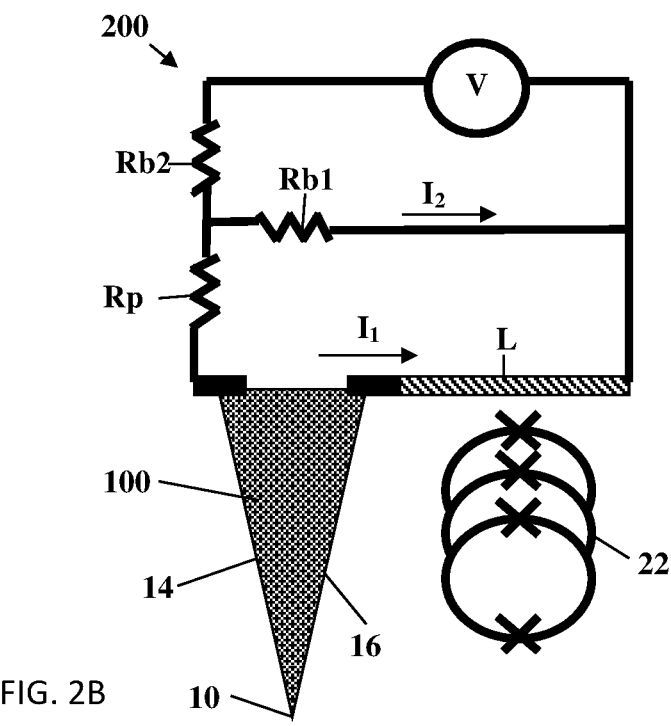

Reference is now made to FIGS. 2A and 2B schematically illustrating the thermal sensor/probe 100 and two exemplary measurement circuits 200 suitable to provide data indicative of sample temperature. As shown in FIG. 2A, the circuit 200 may generally include a variable current supply unit I configured to selectively transmit DC current through the cap 10. The circuit lines and leads are preferably configured such that the cap 10 is the first element to break its superconducting state. As long as the cap 10 is in its superconductive state, all current flows through the main circuit $I_1$ and through the cap 10. When the current reaches the cap's critical current, the superconductive state of the cap breaks and current flows though the secondary circuit $I_2$. The current through each circuit is generally measured, in this example the current is shown to be measured by a superconducting squid array (SSAA) 22 detecting magnetic field variations generated by the current flow through the circuit (exemplified in the figure by coil L). FIG. 2B exemplified the use of a voltage supply unit V, in combination with a second bias resistor Rb2.

Figure 3:
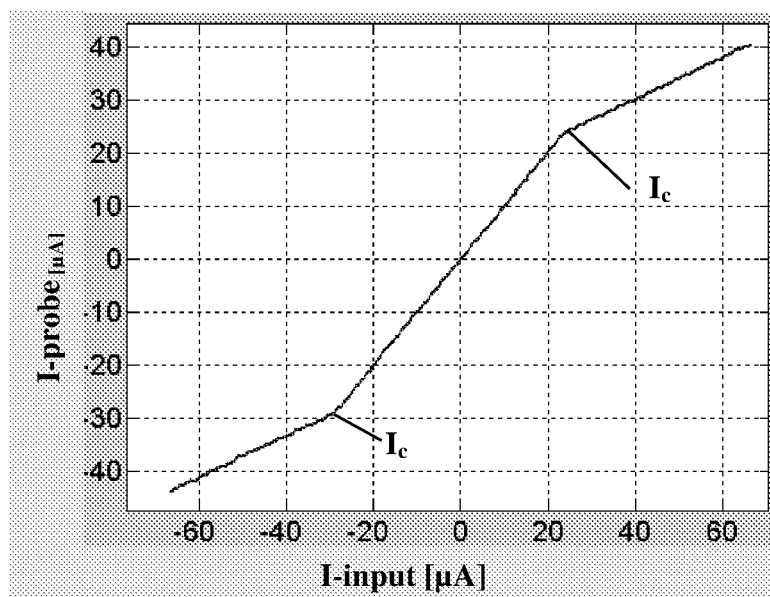
FIG. 3 shows current response of the probe/sensor according to embodiments of the invention.

In this connection, FIG. 3 exemplifies a technique for determining critical current of the circuit 200, which generally indicates the critical current of the cap 10 selected to have lowest critical current. FIG. 3 shows relation between input current as provided by the current supply unit I (or alternatively as measured on bias resistor Rb2 in FIG. 2B) and the current flowing through the probe 100 itself (e.g. as measured by SSAA 22). As shown, for input current being lower than the critical current, the main circuit $I_1$ is essentially superconducting and thus no current is transmitted through the secondary circuit $I_2$ (that includes bias resistor Rb or Rb1). As shown in the figure, for input current below the critical current, I-probe is equal to I-input. When the input current I-input exceeds the critical current, resistance appears in the main circuit $I_1$ and a portion of the current flows through the secondary circuit $I_2$. This is shown in the figure in that I-probe becomes smaller than I-input and the plot curve changes indicating the critical current $I_c$.

Figure 4A:
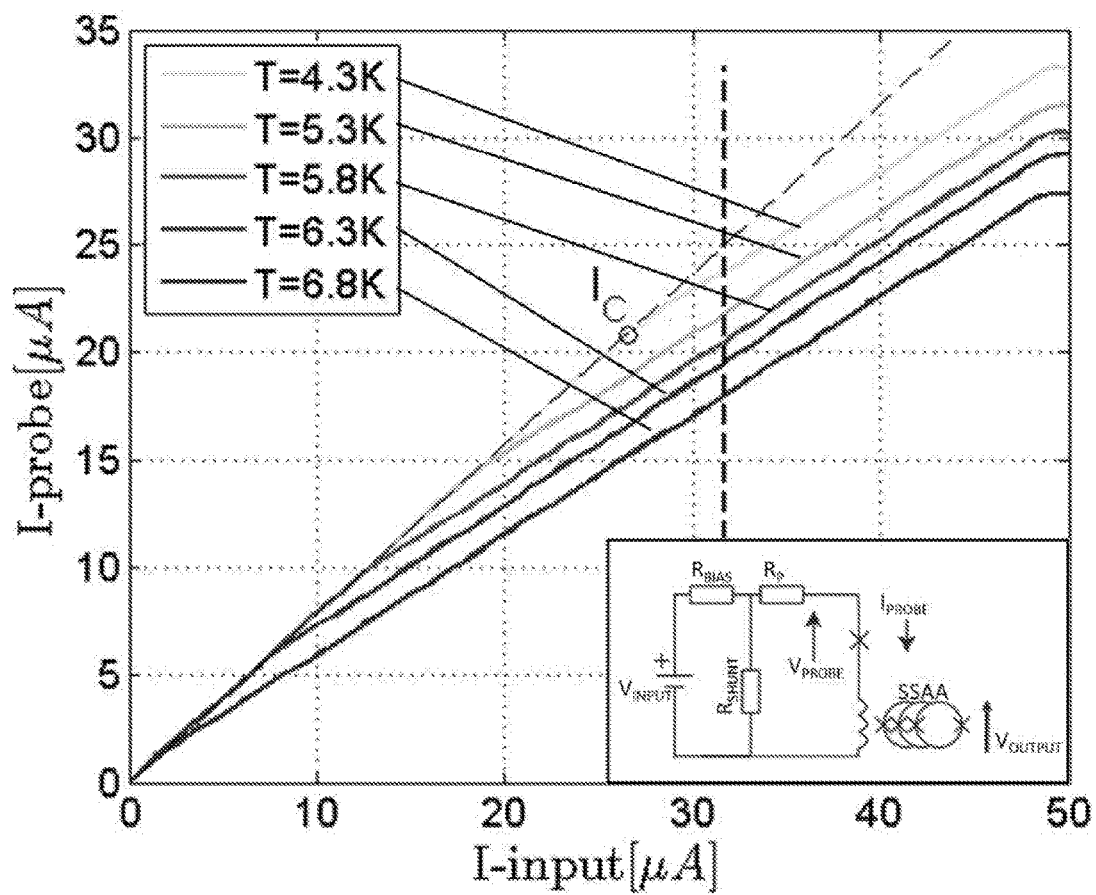
FIGS. 4A to 4C exemplify measurement technique (FIG. 4A), thermal response (FIG. 4B) and noise level (FIG. 4C) of a probe/sensor according to some embodiments of the present invention.
Figure 4B:
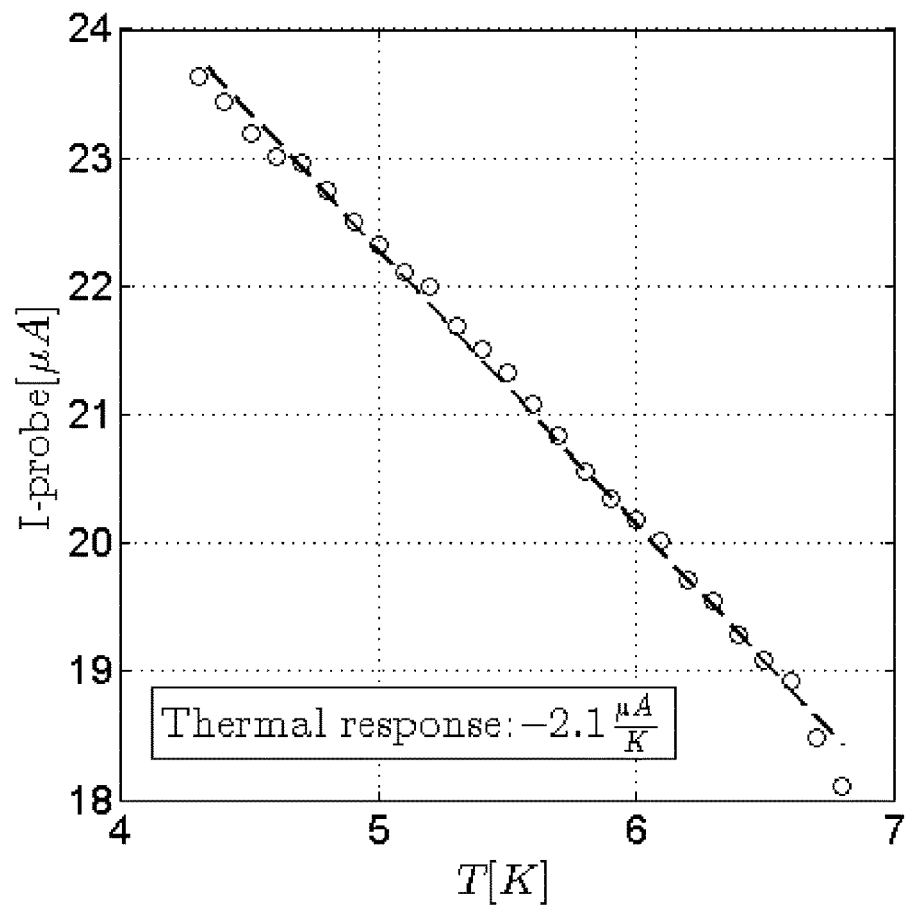
Figure 4C:
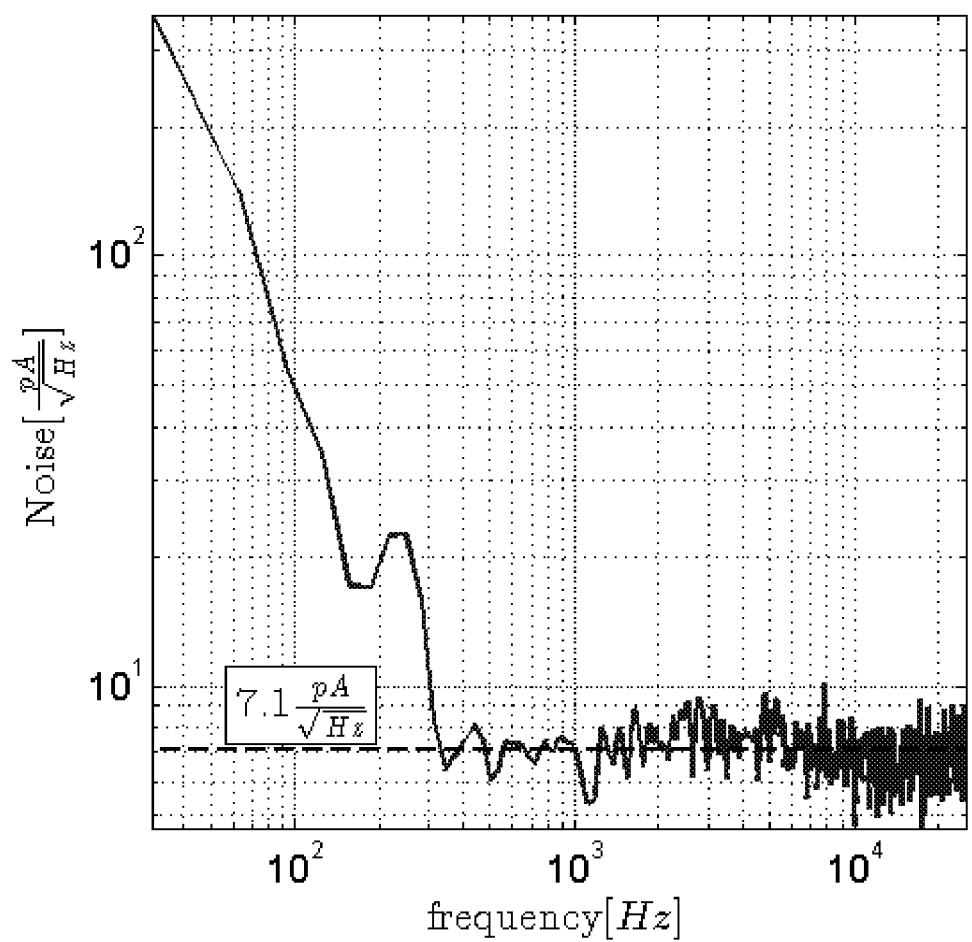

Additionally, FIGS. 4A to 4C exemplify experimental thermal operation based on critical current variation with respect to the probe temperature utilizing a Pb based probe. FIG. 4A shows probe current with respect to input voltage (corresponding to the circuit of FIG. 2B) for different probe temperatures between 4.28K and 6.87K, using Pb (lead) superconductive cap. FIG. 4B shows the measured critical current as a function of the temperature. This graph shows substantially linear dependence of the critical current on the probe temperature, indicating that such measurement technique provides reliable data indicative of the probe temperature. Specifically, as shown the thermal response of the probe sensor used in this example is about $$\frac{2 \text{ μA}}{K}$$

for a fixed bias voltage. More specifically, the thermal response is $$\frac{2.1 \text{ μA}}{K}$$

and may generally vary in accordance with material selection and geometrical configuration of the probe sensor 100. FIG. 4C shows noise levels achieved by the probe 100. The noise level provided by the probe is shown to be about $$\frac{7 \text{ pA}}{\sqrt{Hz}}$$

$$\left(\text{more specifically } \frac{7.1\,\text{pA}}{\sqrt{\text{Hz}}}\right)$$

as shown in the figure, and of about $$\frac{5\,\text{pA}}{\sqrt{\text{Hz}}}$$

in an additional measurement. This, taken into account together with the thermal response shown in FIG. 4B provides thermal resolution of $$\frac{3\,\mu\text{K}}{\sqrt{\text{Hz}}}$$

and even $$\frac{2\,\mu\text{K}}{\sqrt{\text{Hz}}}$$

provides high sensitivity and efficient temperature measurement. More specifically, the probe of the present invention may provide thermal measurements at a temperature resolution of 2-3 micro-Kelvin (with 1 second integration time), additionally, thermal resolution of below $$\frac{1\,\mu\text{K}}{\sqrt{\text{Hz}}}$$

has been experimentally achieved.

Therefore, the probe configuration as shown in FIG. 1 provides ultra sensitive thermal sensor for temperatures below critical temperature of the cap material. Generally the probe/sensor 100 is capable of reaching thermal noise levels of the order of $$\frac{1\,\mu\text{K}}{\sqrt{\text{Hz}}}$$

and lower with a typical bandwidth of 200 kHz. It should be noted that the bandwidth may vary in accordance with characteristics of the sample being measured. Generally, the theoretical limit of the sensor probe in the above described configuration is in the range of 100 MHz. It should be noted that the bandwidth may generally depend of tip-sample heat conduction, which will be described further below.

In this connection, reference is made again to FIG. 4A. The figure shows probe current vs. input current curves for different temperatures of the probe. Generally the temperature measurement may utilize determining the probe current vs. input current curve. However, the thermal measurement system may be calibrated for determining the sensed temperature in accordance with the current curves as shown in FIG. 4A for different probe temperatures. In this connection, the probe may be operated by transmission of a fixed input current (I-input), which may typically be higher than the critical current of the probe, as shown by dotted line ML for measurement line. This provides temperature measurement as a direct consequence of the probe current, as shown in FIG. 4B. This reduces the measurement time at each scanning point as the measured quantity may be the probe current and no current sweeping is required.

As indicated above, the resolution of temperature measurements by the probe sensor of the invention may be varied in accordance with measurement integration time. More specifically, the temperature may be averaged over time to eliminate noise over the signal, and improve the reading accuracy. Thus, the sensor 100 of the present invention may provide greater temperature resolution at the cost of slower scan time, and/or slower response time. Generally performing measurements utilizing integration time of up to 30 seconds, the sensor 100 described above may provide temperature measurement with resolution of up to order of $10^{-7}$K.

Also, it should be noted that superconductivity has been shown to be a state of matter. Thus the actual selection of material varies the working temperature range, but the operational principles of the probe remain similar. For example, the probe cap and leads used in the system to provide the results shown in FIGS. 3 and 4A-4C is made of Pb cap and leads. This provides operational temperatures below 7K. According to other embodiments of the invention, superconductive materials, metals such as Al, Ti, La, Mo, Nb, In, Ir, Ga, Cd, Hg, Hf, Os, Pa, Re, Ru, Sn, Ta, Th, Tl, Tc, U, V, W, Zn, or Zr; as well as compounds such as $Ba_8Si_{46}$, $C_6Ca$, $C_6Li_3Ca_2$, $C_8K$, $C_8KHg$, $C_6K$, $C_3K$, $C_3Li$, $C_2Li$, $C_3Na$, $C_2Na$, $C_8Rb$, $C_6Sr$, $C_6Yb$, $C_{60}Cs_2Rb$, $C_{60}K_3$, $C_{60}RbX$, Diamond:B, $FeB_4$, InN, $In_2O_3$, Si:B, SiC:B, SiC:Al, $LaB_6$, $Nb_3Al$, $Nb_3Ge$, NbO, NbN, $Nb_3Sn$, $NbSe_2$, NbTi, $YB_6$, TiN, ZrN, $ZrB_{12}$; and also high critical temperature superconductor such as Cuprate superconductors, iron-based superconductors and magnesium diboride may also be used, as well as combinations of these materials.

The probe was fabricated on an apex of a hollow quartz tube pulled into a very sharp pipette. This is to provide suitable geometry for use in scanning probe microscopy. The superconductive films were deposited in three self-aligned steps, resulting in two superconductive leads 12 and 14 connected to a superconductive cap 10. It should be noted that the cap 10 itself may be of any geometrical structure. For example, the cap may be in the form of a small circular region, a loop formed by closed circle, or any other shape. However, as indicated above the configuration and material composition of the cap are selected such that critical current supported thereby is lower with respect to critical current supported by the leads.

Figure 5:
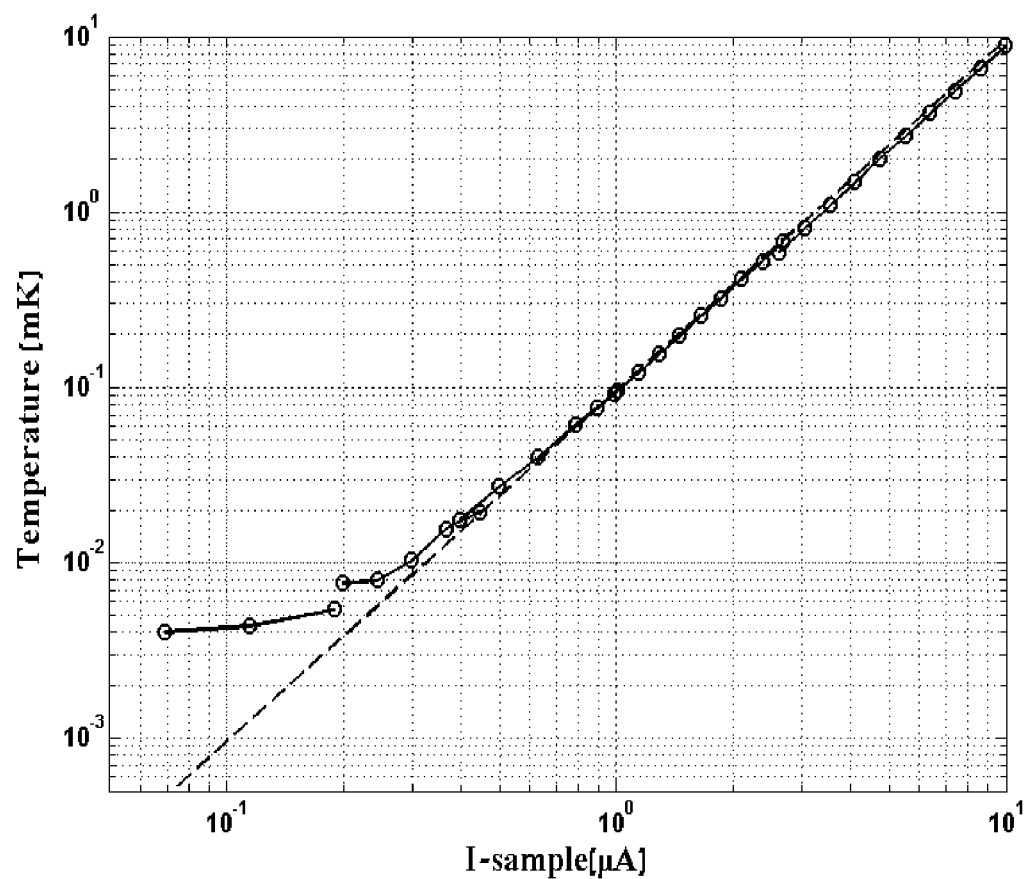
FIG. 5 shows thermal measurement of a test sample.

Thus, as shown above, the thermal sensor/probe 100 of provides a combination of high thermal response with low noise levels. Reference is made to FIG. 5 showing thermal measurement of a 170Ω nanoresistor (nanoflake). In this connection, the probe was placed at a fixed location, about 200 nm above the nanoresistor to provide thermal measurements of the resistor while current is transmitted through the resistor. Generally, the resistor acts as a heat source measured by the probe. Selected AC currents were transmitted through the resistor, and the signal was detected using a lock-in amplifier set on an integration time of 300 ms. FIG. 5 shows the resulting temperature reading by the probe 10 as a function of current.

Figure 6:
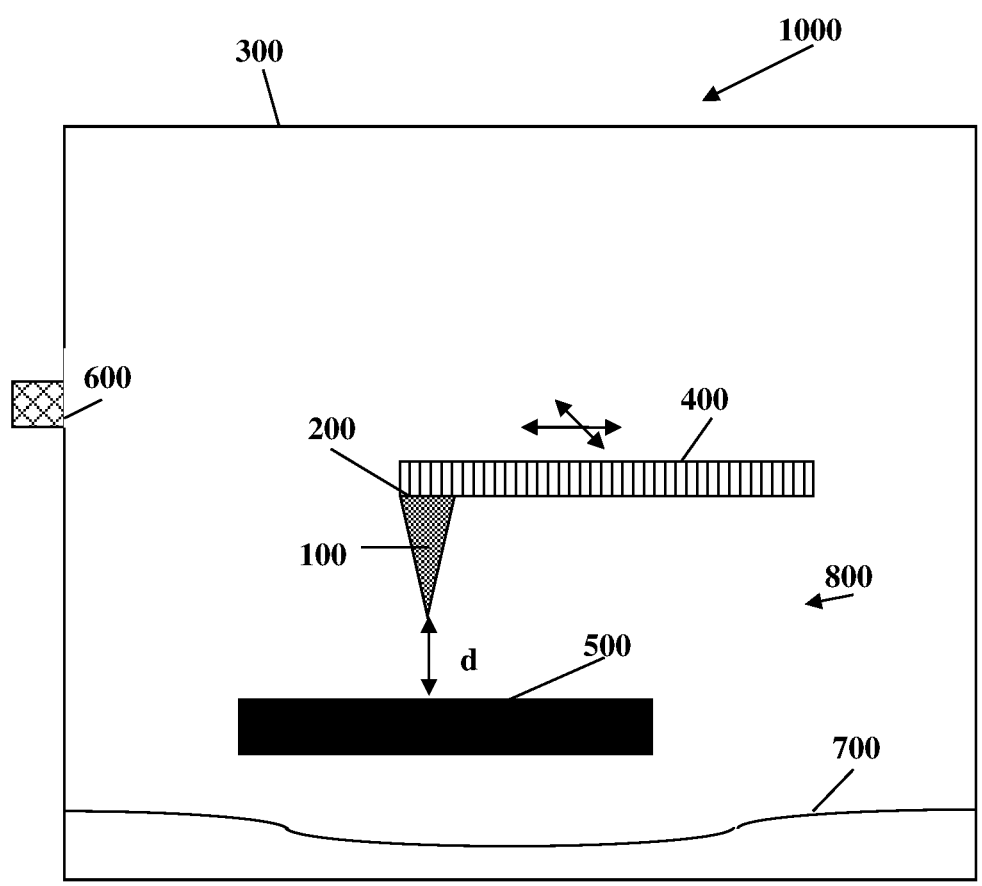
FIG. 6 illustrates a thermal scanning microscope system according to some embodiments of the present invention.

The high sensitivity of the probe 100 allows non-contact thermal measurements. It should be noted that at cryogenic conditions together with low pressure, radiation and heat exchange are generally limited. Generally, the probe/sensor 100 and its corresponding measurement circuit 200 may be mounted on a scanning microscope tip. The microscope is operable inside a vacuum chamber maintaining a predetermined pressure and temperature range for operation of the probe. Reference is made to FIG. 6 illustrating a thermal scanning microscope system 1000 as described herein. The thermal microscope system 1000 includes the above describe probe 100 operated by a measuring circuit 200 and mounted on a scanning tip 400 movable with respect to a sample located on a sample holder 500. As described, the microscope operates within a vacuum chamber 300, which is initially evacuated using a vacuum pump 600. A controlled amount of exchange gas 800 is later inserted into the chamber 300 to enable heat transfer between the sample of inspection and the tip 400. It should be noted that the vacuum pump 600 may be continuously operated to maintain predetermined pressure in the chamber 300, or stop its operation when desired pressure is achieved to allow desired amount of exchange gas to be in the chamber 300 and enable heat transfer. Additionally, gas introduction into the chamber may be controlled to limit the amount of gas and its composition within the chamber 300. The vacuum chamber 300 may also include a thermal pool 700 configured to maintain operation temperature below critical temperature for operation of the probe 100. For example, in case of Pb based probe as describe above, the thermal pool 700 may include liquid He for providing temperature at a region of 4.2K. Utilizing other superconducting material, the thermal pool 700 may include liquid Nitrogen or any other suitable technique for maintaining superconducting temperatures. To provide thermal exchange between the sample and the probe, the vacuum chamber may include certain levels of exchange gas 800 (e.g., He, $N_2$, $CO_2$, Ar etc.). The exchange gas 800 may be introduced into the chamber 300 for thermal stabilization of the probe 100.

The exchange gas 800 generally acts as a heat transfer medium between the sample and the cap. In this connection, thermal exchange properties of low pressure gas may generally be determined by a corresponding mean free path of the gas particles (atoms or molecules). For example, for He atoms, the mean free path is given in μm in accordance with the formula:

$$l_{mfp} = 0.287 \frac{(T[K])^{2.147}}{P[mBar]} \quad \text{(equation 1)}$$

where is the mean free path in microns, T[K] is the gas temperature in Kelvin and P[mBar] is the gas pressure in milliBar. This provides, for exchange gas pressure in the order of 1 mbar and liquid He temperatures of about 4.2K mean free path of about $l_{mfp} \approx 6$ μm. Thus, for distances much larger than $l_{mfp}$ the heat conductivity through the exchange gas is mainly governed by the hydrodynamic regime, and is substantially pressure independent. At such distances, the heat conductivity is generally inversely proportional to the distance. On the other hand, for distances lower than $l_{mfp}$ heat conductivity is provided by direct molecular interactions (molecular regime). More specifically, the exchange gas particles flow ballistically from the sample until hitting the cap 10 of the probe 100. In this regime the heat conductivity is expected to be proportional to the gas pressure and independent of the cap-sample distance d.

Figure 7A:
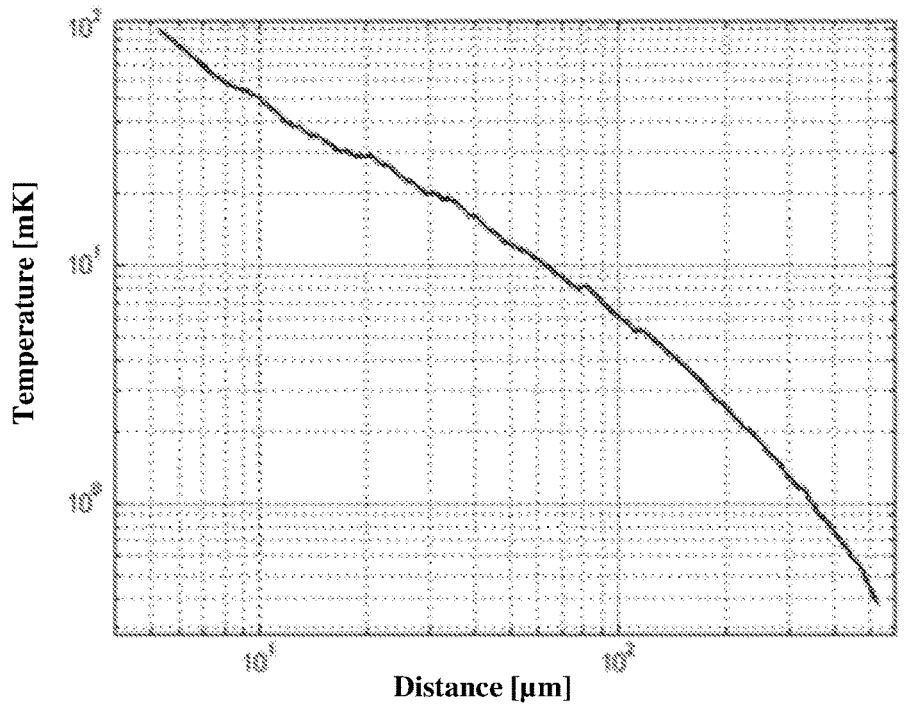
FIGS. 7A and 7B show thermal signal measures as a function of distance (FIG. 7A) and pressure (FIG. 7B) from a test sample.
Figure 7B:
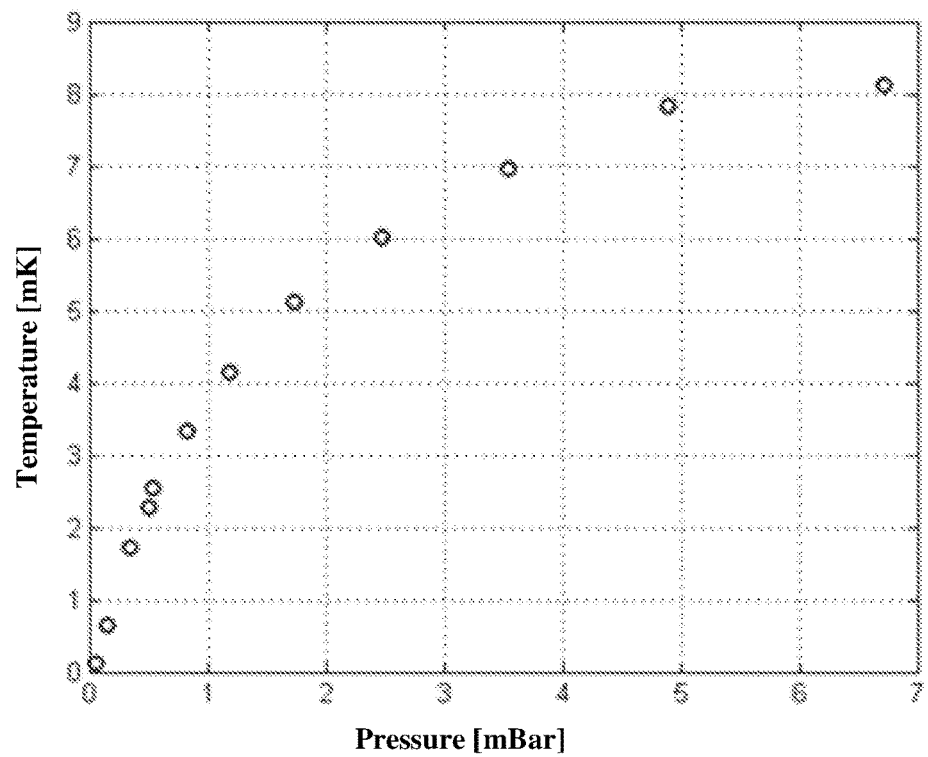

Thermal measurements in the hydrodynamic and molecular regimes are exemplified in FIGS. 7A and 7B. These figures show thermal measurement at different distances d from a heat source sample providing a 0.5 μW signal. FIG. 7A shows measured temperature of the heat source as a function of distance from the sample. FIG. 7B shows measured temperature of a 10 nW source at a fixed distance (200 nm) as a function of the pressure in the chamber. In both measurements an AC current at 61.5 Hz and 3.13 KHz respectively flows through a sample and the thermal signal is read by a lock-in amplifier. As shown in the figures, for probe-sample distances in the hydrodynamic regime, the heat flow from the sample to the probe depends inversely on the distance. More specifically, for accurate thermal measurements the probe should be in close vicinity to the sample. As shown in FIG. 7B, at pressure of about 6-7 mBar, the reading of the sensor reaches saturation. This occurs as the heat flow from the sample through the gas becomes more dominant than the heat flow from the probe cap 10 to the supporting elements thereof (e.g. the elongated support structure 12 and the bulk) and to the environment. This shows that even though the cap 10 of the sensor may not be in physical contact with the sample, sufficient heat flow can be achieved to enable the thermal sensor 100 to detect local thermal variation of the sample. It should be noted that this sensitivity can be achieved since the probe of the present invention is preferably configured such that the thermal resistance between the cap and the sample is significantly lower with respect to the thermal resistance between the cap and its supporting structure that actually provides a thermal (heat) bath. This, in turn, is provided by proper configuration of the elongated support structure 12 having a narrow elongated geometry, which on top of directly affecting the resistance, also reduces thermal conductivity relative to the corresponding bulk value.

Example 1

Figure 8A:
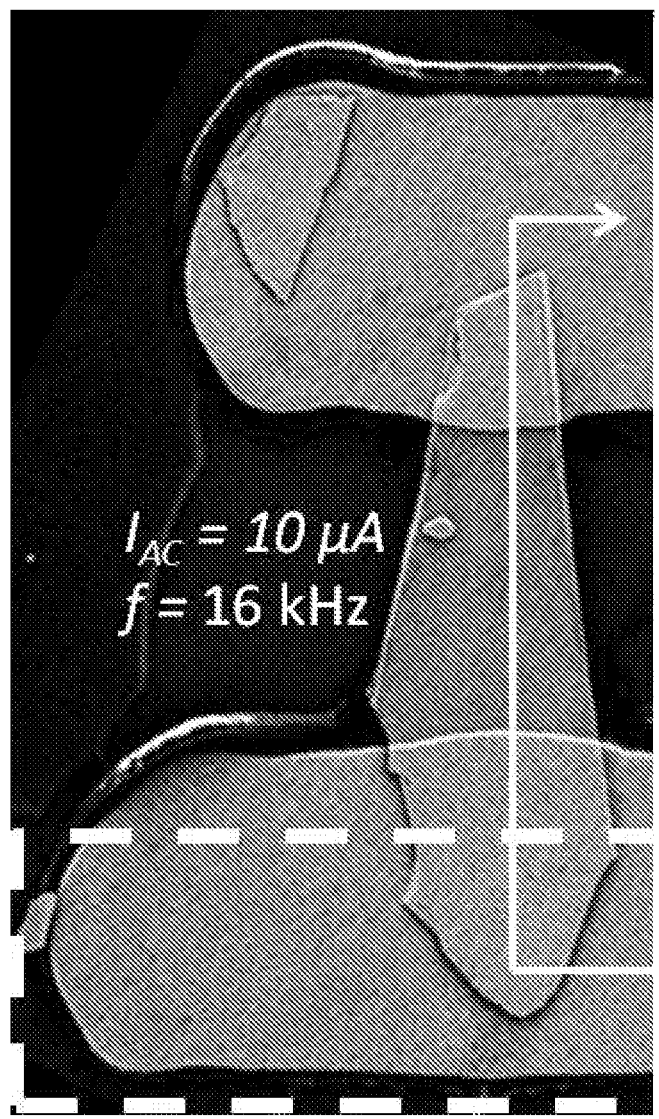
FIGS. 8A to 8C show thermal mapping of a test sample utilizing the technique of the present invention.
Figure 8B:
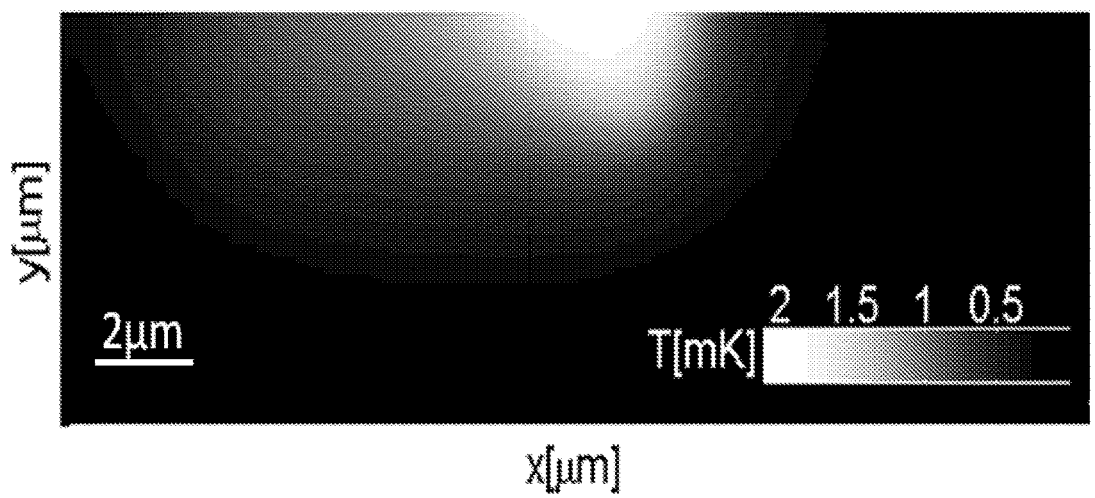
Figure 8C:
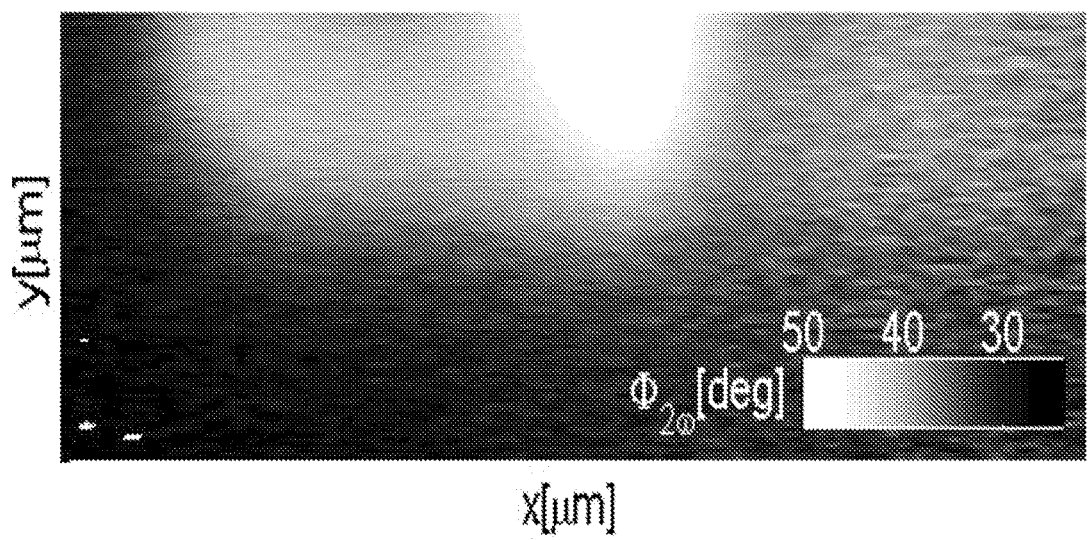

To demonstrate the thermal imaging capabilities of the device a suspended $Bi_2Se_3$ nano-flake device has been fabricated, using an exfoliation technique on top of a Si—$SiO_2$ wafer. Optical lithography was used to deposit gold leads, and the $SiO_2$ layer was partially etched to make the flake suspended above the substrate. The flake showed a resistance of 170Ω. An AC current of 10 μA at a frequency of 16 KHz flows through the flake. This corresponds to a power of 17 nW; this power has a DC component and an additional component at the second harmonic of the excitation, or 32 KHz in this case. By using a lock-in amplification technique and isolating the second harmonic of the sensor signal while scanning over the sample, a thermal image of the nano-flake was measured. The measured thermal signal has two components that are measured individually during scanning. The first component is the amplitude, which describes the magnitude of the local temperature variation, and the second component is the phase (relative to the excitation signal), which provides information about the time delay of the heat propagation in the sample. In this connection, FIG. 8B shows an image of the measured amplitude of the temperature variation while FIG. 8C shows an image of the phase of the measured signal. These two images provide different and complementary information about temperature distribution of the sample. As shown in FIG. 8C, the phase signal accurately traces the topography of the device. However, FIG. 8B shows a significant signal in the left part of the gold lead, even though no current flows there, as opposed to the right side where the current flows, but the thermal signal is significantly smaller. This is caused by the superior heat conduction of the gold lead, and its thermal anchoring to the liquid helium bath that reduces the increase in temperature of the gold lead.

In this connection it should be noted that the bandwidth of the sensor 100 is a measure of the smallest temporal variations in temperature that the sensor can detect. The above example shows the use of the sensor 100 for detection of thermal variations of a given sample, varying with frequencies of up to few tens of 10 kHz. It should, however, be noted that this frequency range is a result of thermal time scales in the sample, and not an actual limitation of the probe. Generally, the probe 100 of the present invention may provide thermal measurements at bandwidth of the order of a few MHz, and is theoretically limited by a bandwidth of 100 MHz. This provides high thermal as well as high temporal resolution for temperature variation detection.

It should be noted that the phase signal exemplified in FIG. 8C provides data about temporal heat propagation within the sample. More specifically, when energy is pumped through the sample in pulses, e.g. heating with alternating current (AC), heat is generated at regions where current flows through, and diffuses to other regions. Utilizing the phase relation between the AC heating current and the detected signal provides data indicative of time scales required for heat transfer between regions of the sample. This is generally of great value, providing simple measurements for heat transfer characteristics of the sample within a single thermal scanning measurement.

Thus, as described above, the present invention provides a novel sensor structure and technique enabling thermal measurements and mapping of a sample while avoiding physical contact with the sample. Additionally, the invention provides a novel thermal microscope system and technique for thermal imaging of a sample.

Cap Cooling Mode

According to an embodiment of the present invention, when a high bias voltage is deliberately applied to the cap so that the current flowing through the cap is considerably above its critical current, heat is dissipated in the apex of the cap. This heat is removed by conduction through the exchange gas and transferred to the sample. When scanning a sample in this mode close to the sample surface, even without dissipation of heat from the sample, the cap temperature will vary as it passes along different regions of the sample that have different local thermal conductance values.

In this embodiment, the device can be used for thermal conductivity imaging, and can resolve minute variations in the thermal characteristics of the sample from one region to another. In a non-limiting example illustrated in FIG. 9, the device resolves the boundary between a monolayer and bi-layer of graphene on the surface of a silicon oxide substrate sample. In a related embodiment, the device may be used for failure detection.

Figure 9:
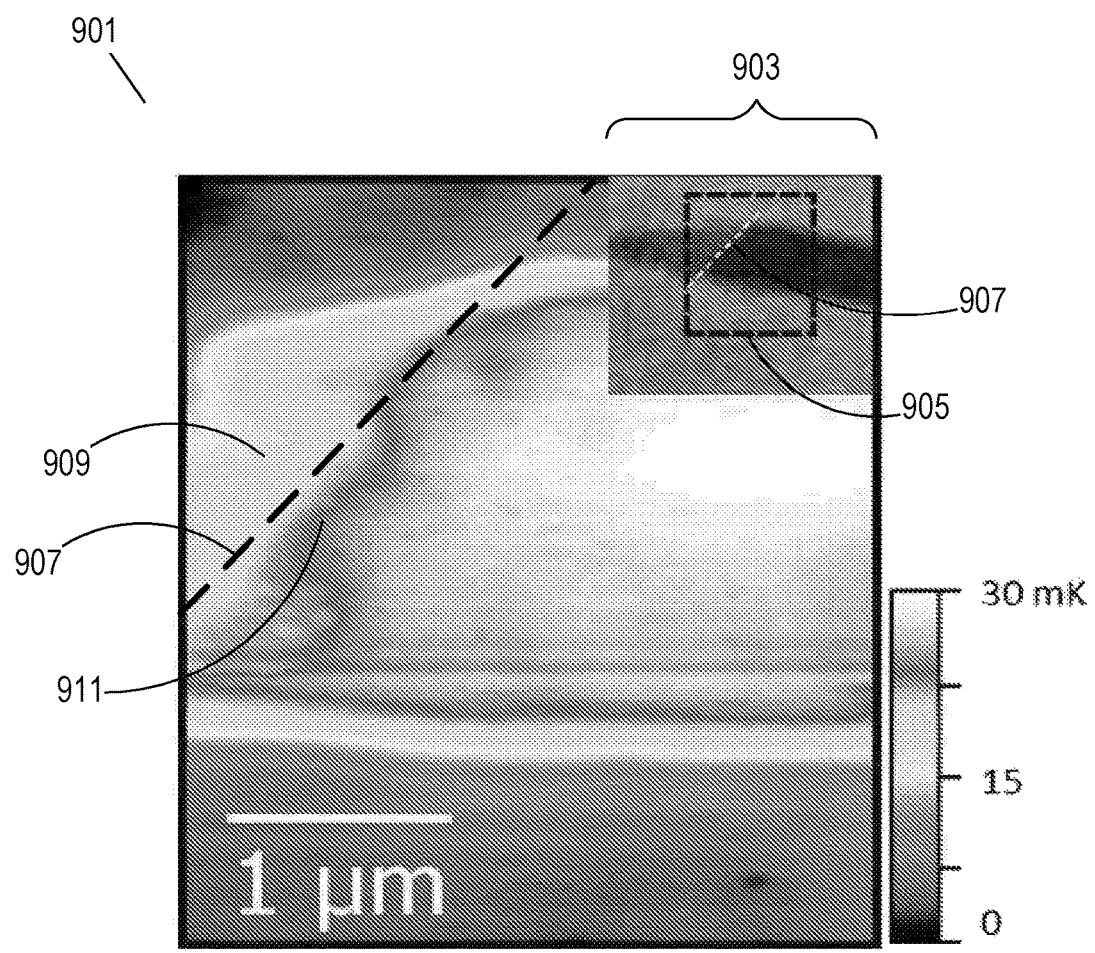
FIG. 9 shows thermal conductivity mapping of a test sample utilizing a technique according to an embodiment of the present invention.

FIG. 9 shows a scan 901 of a sample of a grapheme device on a silicon oxide substrate as provided by this embodiment employing cooling mode thermal imaging. An inset shows an optical image 903 of the sample, with the scan region delineated by a dashed line 905. A dashed line 907 shown in both scan 901 and optical image 903 marks the boundary between a graphene monolayer 909 and a graphene bi-layer 911. The boundary is clearly visible on scan 901.

What is claimed is:

1. A device for use in thermal microscopy, the device comprising:
   an elongated support structure having a near end for attachment to an external connection, and a far end;
   an electrically conductive cap located at the far end of the support structure;
   at least two spaced apart elongated conductive leads extending from the electrically conductive cap along the support structure to the near end thereof and in electrical contact with the electrically conductive cap, wherein the electrically conductive cap and the at least two elongated conductive leads define a path for transmission of electric current through the cap; and
   wherein the electrically conductive cap and elongated conductive leads are of a selected material composition such that they are in a superconductive state at a first predetermined condition.

2. The device of claim 1, wherein, when in the superconductive state, the electrically conductive cap is configured to support a first critical current, and the elongated conductive leads are configured to support a second critical current greater than the first critical current.

3. The device of claim 2, wherein the electrically conductive cap is configured to have a first cross section along a path of electrical current and the elongated conductive leads are configured to have a second cross section along a path of electrical current, the second cross section having a greater area than the first cross section.

4. The device of claim 2, wherein the electrically conductive cap and the elongated conductive leads are of selected material compositions to provide the first and second critical currents.

5. The device of claim 1, wherein the device is of nanometric dimension.

6. The device of claim 5, wherein the electrically conductive cap is configured with a diameter of less than 300 nm.

7. The device of claim 5, wherein the electrically conductive cap is configured with a diameter of less than 100 nm.

8. The device of claim 1, wherein the device is configured for scanning probe thermal microscopy.

9. The device of claim 1, wherein the electrically conductive cap and the elongated conductive leads comprise material composition selected from type I superconductors or type II superconductors.

10. The device of claim 1, wherein the elongated support structure is configured as conical structure.

11. The device of claim 1, wherein the elongated support structure is configured from pulled quartz rod.

12. A sensor device comprising:
    a probe carrying a non-invasive thermal sensor, the probe comprising:
      a support structure configured to be carried by connection to a near end thereof and carrying a superconductive cap attached to a far end thereof, and
      at least two elongated superconductive leads connected to the superconductive cap at a far end thereof and providing corresponding electrically conductive ports at near end to thereby allow current transmission to the cap;
    wherein the superconductive cap has a first critical current value and the superconductive leads have a second critical current value higher than the first critical current value.

13. The device of claim 12, configured to provide thermal measurements of a sample with the cap at a distance greater than 10 nanometers from the sample.

14. The device of claim 12, configured to provide thermal measurements of a sample with the cap at a distance greater than 1 micro-meter from the sample.

15. A system comprising:
    a scanning unit carrying a sensor probe,
      the scanning unit configured to selectively move the probe along a surface of a sample, the sensor probe comprising an elongated support structure carried on a near end thereof by the scanning unit and carrying an electrically conductive cap on a far end thereof; and at least two elongated conductive leads electrically connected to the cap, wherein the electrically conductive cap and the at least two elongated conductive leads define a path for transmission of electric current through the cap;

wherein the sensor probe is configured for thermal measurements of the surface of the sample; and wherein the electrically conductive cap and elongated conductive leads are of a selected material composition such that they are in a superconductive state at a predetermined condition.

16. The system of claim 15, wherein the sensor probe is configured for thermal measurements of the surface of the sample without being in physical contact with the surface.

17. The system of claim 15, wherein the scanning unit is configured for:
holding the probe at a fixed location; and
varying a location of a sample holder carrying the sample.

18. The system of claim 15, further comprising a vacuum chamber configured for:
holding the sample to be scanned; and
performing the scan therein.

19. The system of claim 15, wherein the sensor probe is configured to determined temperature variation of the sample in a cryogenic temperature range.

20. A method for thermal imaging a sample, the method comprising:
providing a superconductive cap on the tip of an elongated probe, the superconductive cap having a first critical current value and being in close proximity to the sample; and
transmitting an electrical current through the cap to determine a variation in a critical current thereof, the variation in the critical current being indicative of a local temperature of the sample.

21. The method of claim 20, further comprising scanning the surface of the sample to provide a temperature map thereof.

22. The method of claim 20, wherein the transmitting the electrical current through the cap comprises:
gradually increasing the electrical current;
measuring a resistance to the electrical current through the cap; and
determining a critical current value of the cap from the measuring.

23. The method of claim 20, wherein the transmitting electrical current through the cap comprises:
transmitting a fixed current through the probe; and
determining the critical current based on a portion of the fixed current flowing through the cap.

24. The method of claim 20, wherein the close proximity is a distance greater than 10 nm from the sample.

25. The method of claim 20, further comprising:
inducing a periodical thermal variation into the sample; and
periodically detecting the critical current of the superconductive cap to determine an amplitude and a phase indicative of temperature and heat propagation in the sample.

26. The method of claim 25, wherein the periodically detecting the critical current comprises:
detecting the critical current at a measurement frequency higher than 1 KHz; and
thereby providing a thermal measurement at a bandwidth greater than 1 KHz.

27. The method of claim 25, wherein the periodically detecting the critical current comprises:
detecting the critical current at a measurement frequency higher than 100 KHz; and
thereby providing a thermal measurement at a bandwidth greater than 100 KHz.

28. The method of claim 25, wherein the periodically detecting the critical current comprises:
detecting the critical current at a measurement frequency higher than 10 MHz; and
thereby providing a thermal measurement at a bandwidth greater than 10 MHz.

29. The method of claim 20, further comprising:
Applying a high bias voltage to the cap so that the current flowing through the cap is above the critical current, thereby causing heat to be dissipated in the cap and partially transferred to the sample;
wherein the variation in the critical current indicative of the cap temperature is also indicative of a local thermal conductance of the sample.

30. The device of claim 1, wherein the cap is an integral part of the support structure.

31. The device of claim 1, wherein at least one lead is an integral part of the support structure.

32. The device of claim 1, wherein the electrically conductive cap and elongated conductive leads are of a selected material composition such that at a second predetermined condition the elongated conductive leads are in a superconductive state and the electrically conductive cap is not in a superconductive state.

33. The device of claim 1, wherein the electrically conductive cap and elongated conductive leads are of a selected material composition such that at a second predetermined condition the electrically conductive cap is in a superconductive state and at least one of the elongated conductive leads is not in a superconductive state.

* * * * *